(12) United States Patent
Andino

(10) Patent No.: US 9,604,034 B2
(45) Date of Patent: *Mar. 28, 2017

(54) ANCHORING SYSTEM

(71) Applicant: C. R. Bard, Inc., Murray Hill, NJ (US)

(72) Inventor: Rafael V. Andino, Grayson, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 210 days.

This patent is subject to a terminal disclaimer.

(21) Appl. No.: 14/557,904

(22) Filed: Dec. 2, 2014

(65) Prior Publication Data

US 2015/0088076 A1  Mar. 26, 2015

Related U.S. Application Data

(63) Continuation of application No. 13/452,291, filed on Apr. 20, 2012, now Pat. No. 8,900,196.

(60) Provisional application No. 61/478,027, filed on Apr. 21, 2011.

(51) Int. Cl.

| *A61M 5/32* | (2006.01) |
|---|---|
| *A61M 5/00* | (2006.01) |
| *A61M 25/02* | (2006.01) |
| *A61M 5/14* | (2006.01) |
| *A61M 16/00* | (2006.01) |
| *A61B 50/20* | (2016.01) |

(52) U.S. Cl.
CPC .............. *A61M 25/02* (2013.01); *A61B 50/20* (2016.02); *A61M 5/1418* (2013.01); *A61M 16/0003* (2014.02); *A61M 2025/024* (2013.01); *A61M 2209/082* (2013.01); *A61M 2209/088* (2013.01)

(58) Field of Classification Search
CPC .......... A61M 2209/082; A61M 5/1418; A61M 2025/024; A61M 25/02; A61M 39/28; A61M 39/287; A61B 50/20
See application file for complete search history.

(56) References Cited

U.S. PATENT DOCUMENTS

| 2,402,306 A | 6/1946 | Turkel |
|---|---|---|
| 2,525,398 A | 10/1950 | Collins |
| 2,533,961 A | 12/1950 | Rousseau et al. |
| 2,707,953 A | 5/1955 | Ryan |

(Continued)

FOREIGN PATENT DOCUMENTS

| CA | 1311977 C | 12/1992 |
|---|---|---|
| CA | 1318824 C | 6/1993 |

(Continued)

OTHER PUBLICATIONS

ARROW International, Inc. Multiple-Lumen Central Venous Catheterization Product with ARROWgard™ Antiseptic Surface, 6 pgs., K-24703-1008 (Apr. 1994).

(Continued)

*Primary Examiner* — Rebecca E Eisenberg
(74) *Attorney, Agent, or Firm* — Rutan & Tucker, LLP

(57) ABSTRACT

A retainer comprises a first member and a second member. The first member can define at least a portion of a channel. The channel can have a longitudinal axis and be configured to receive at least a portion of a medical article. The second member can be moveable with respect to the first member, between locked and unlocked positions. The second member can contact the portion of the medical article received by the channel at least when in the locked position so as to inhibit longitudinal movement of the medical article relative to the retainer.

11 Claims, 7 Drawing Sheets

(56) References Cited

U.S. PATENT DOCUMENTS

| | | |
|---|---|---|
| 3,046,984 A | 7/1962 | Eby |
| 3,059,645 A | 10/1962 | Hasbrouck et al. |
| 3,064,648 A | 11/1962 | Bujan |
| 3,167,072 A | 1/1965 | Stone et al. |
| 3,194,235 A | 7/1965 | Cooke |
| 3,245,567 A | 4/1966 | Knight |
| 3,288,137 A | 11/1966 | Lund |
| 3,394,954 A | 7/1968 | Sams |
| 3,482,569 A | 12/1969 | Raaelli, Sr. |
| 3,529,597 A | 9/1970 | Fuzak |
| 3,589,361 A | 6/1971 | Loper et al. |
| 3,602,227 A | 8/1971 | Andrew |
| 3,613,663 A | 10/1971 | Johnson |
| 3,630,195 A | 12/1971 | Santomieri |
| 3,677,250 A | 7/1972 | Thomas |
| 3,686,896 A | 8/1972 | Rutter |
| 3,766,915 A | 10/1973 | Rychlik |
| 3,782,383 A | 1/1974 | Thompson et al. |
| 3,812,851 A | 5/1974 | Rodriguez |
| 3,826,254 A | 7/1974 | Mellor |
| 3,834,380 A | 9/1974 | Boyd |
| 3,856,020 A | 12/1974 | Kovac |
| 3,863,527 A | 2/1975 | Berning |
| 3,863,631 A | 2/1975 | Baldwin |
| 3,900,026 A | 8/1975 | Wagner |
| 3,901,226 A | 8/1975 | Scardenzan |
| 3,906,946 A | 9/1975 | Nordstrom |
| 3,920,001 A | 11/1975 | Edwards |
| 3,942,228 A | 3/1976 | Buckman et al. |
| 3,973,565 A | 8/1976 | Steer |
| 3,993,081 A | 11/1976 | Cussell |
| 4,004,586 A | 1/1977 | Christensen et al. |
| D243,477 S | 2/1977 | Cutruzzula et al. |
| 4,020,835 A | 5/1977 | Nordstrom et al. |
| 4,037,599 A | 7/1977 | Raulerson |
| 4,057,066 A | 11/1977 | Taylor |
| 4,059,105 A | 11/1977 | Cutruzzula et al. |
| 4,079,738 A | 3/1978 | Dunn et al. |
| 4,082,094 A | 4/1978 | Dailey |
| 4,114,618 A | 9/1978 | Vargas |
| 4,116,196 A | 9/1978 | Kaplan et al. |
| 4,123,091 A | 10/1978 | Cosentino et al. |
| 4,129,128 A | 12/1978 | McFarlane |
| 4,133,312 A | 1/1979 | Burd |
| 4,142,527 A | 3/1979 | Garcia |
| 4,161,177 A | 7/1979 | Fuchs |
| 4,165,748 A | 8/1979 | Johnson |
| D252,822 S | 9/1979 | McFarlane |
| 4,170,993 A | 10/1979 | Alvarez |
| 4,170,995 A | 10/1979 | Levine et al. |
| 4,182,455 A | 1/1980 | Zurawin |
| 4,193,174 A | 3/1980 | Stephens |
| 4,194,504 A | 3/1980 | Harms et al. |
| D256,162 S | 7/1980 | Haerr et al. |
| 4,224,937 A | 9/1980 | Gordon |
| 4,230,109 A | 10/1980 | Geiss |
| 4,248,229 A | 2/1981 | Miller |
| 4,250,880 A | 2/1981 | Gordon |
| 4,275,721 A | 6/1981 | Olson |
| 4,284,076 A | 8/1981 | Hall |
| 4,314,568 A | 2/1982 | Loving |
| 4,316,461 A | 2/1982 | Marais et al. |
| 4,324,236 A | 4/1982 | Gordon et al. |
| 4,326,519 A | 4/1982 | D'Alo et al. |
| 4,333,468 A | 6/1982 | Geist |
| 4,356,599 A | 11/1982 | Larson et al. |
| 4,362,156 A | 12/1982 | Feller, Jr. et al. |
| 4,389,754 A | 6/1983 | Sohma |
| 4,392,853 A | 7/1983 | Muto |
| 4,397,647 A | 8/1983 | Gordon |
| 4,398,757 A | 8/1983 | Floyd et al. |
| 4,405,163 A | 9/1983 | Voges et al. |
| 4,405,312 A | 9/1983 | Gross et al. |
| 4,435,174 A | 3/1984 | Redmond et al. |
| 4,435,175 A | 3/1984 | Friden |
| 4,439,193 A | 3/1984 | Larkin |
| D273,993 S | 5/1984 | Schulte et al. |
| 4,449,975 A | 5/1984 | Perry |
| 4,453,933 A | 6/1984 | Speaker |
| 4,470,410 A | 9/1984 | Elliott |
| 4,474,559 A | 10/1984 | Steiger |
| 4,480,639 A | 11/1984 | Peterson et al. |
| 4,484,913 A | 11/1984 | Swauger |
| 4,500,338 A | 2/1985 | Young et al. |
| 4,516,968 A | 5/1985 | Marshall et al. |
| 4,517,971 A | 5/1985 | Sorbonne |
| 4,533,349 A | 8/1985 | Bark |
| 4,561,857 A | 12/1985 | Sacks |
| 4,563,177 A | 1/1986 | Kamen |
| 4,583,976 A | 4/1986 | Ferguson |
| 4,585,435 A | 4/1986 | Vaillancourt |
| 4,585,444 A | 4/1986 | Harris |
| 4,621,029 A | 11/1986 | Kawaguchi |
| 4,623,102 A | 11/1986 | Hough, Jr. |
| 4,627,842 A | 12/1986 | Katz |
| 4,631,056 A | 12/1986 | Dye |
| 4,632,670 A | 12/1986 | Mueller, Jr. |
| 4,633,863 A | 1/1987 | Filips et al. |
| 4,636,552 A | 1/1987 | Gay et al. |
| 4,645,492 A | 2/1987 | Weeks |
| 4,650,473 A | 3/1987 | Bartholomew et al. |
| 4,659,329 A | 4/1987 | Annis |
| 4,660,555 A | 4/1987 | Payton |
| 4,666,434 A | 5/1987 | Kaufman |
| 4,669,458 A | 6/1987 | Abraham et al. |
| 4,683,882 A | 8/1987 | Laird |
| 4,693,710 A | 9/1987 | McCool |
| 4,699,616 A | 10/1987 | Nowak et al. |
| 4,711,636 A | 12/1987 | Bierman |
| 4,723,948 A | 2/1988 | Clark et al. |
| 4,733,666 A | 3/1988 | Mercer, Jr. |
| 4,737,143 A | 4/1988 | Russell |
| 4,742,824 A | 5/1988 | Payton et al. |
| 4,743,231 A | 5/1988 | Kay et al. |
| 4,752,292 A | 6/1988 | Lopez et al. |
| 4,775,121 A | 10/1988 | Carty |
| 4,792,163 A | 12/1988 | Kulle |
| 4,795,429 A | 1/1989 | Feldstein |
| 4,808,162 A | 2/1989 | Oliver |
| 4,822,342 A | 4/1989 | Brawner |
| 4,826,486 A | 5/1989 | Palsrok et al. |
| 4,832,019 A | 5/1989 | Weinstein et al. |
| 4,834,702 A | 5/1989 | Rocco |
| 4,834,716 A | 5/1989 | Ogle, II |
| 4,838,858 A | 6/1989 | Wortham et al. |
| D302,304 S | 7/1989 | Kulle et al. |
| 4,846,807 A | 7/1989 | Safadago |
| 4,852,844 A | 8/1989 | Villaveces |
| 4,857,058 A | 8/1989 | Payton |
| 4,863,432 A | 9/1989 | Kvalo |
| 4,878,897 A | 11/1989 | Katzin |
| 4,880,412 A | 11/1989 | Weiss |
| 4,897,082 A | 1/1990 | Erskine |
| 4,898,587 A | 2/1990 | Mera |
| 4,919,654 A | 4/1990 | Kalt |
| 4,921,199 A | 5/1990 | Villaveces |
| 4,932,943 A | 6/1990 | Nowak |
| 4,934,375 A | 6/1990 | Cole et al. |
| 4,941,882 A | 7/1990 | Ward et al. |
| 4,955,864 A | 9/1990 | Hajduch |
| 4,961,505 A | 10/1990 | Moeller |
| 4,966,582 A | 10/1990 | Sit et al. |
| 4,976,700 A | 12/1990 | Tollini |
| 4,981,469 A | 1/1991 | Whitehouse et al. |
| 4,981,475 A | 1/1991 | Haindl |
| 4,986,815 A | 1/1991 | Schneider |
| 4,997,421 A | 3/1991 | Palsrok et al. |
| 5,024,665 A | 6/1991 | Kaufman |
| 5,037,397 A | 8/1991 | Kalt et al. |
| 5,037,398 A | 8/1991 | Buchanan |
| 5,037,405 A | 8/1991 | Crosby |
| 5,069,206 A | 12/1991 | Crosbie |
| 5,073,170 A | 12/1991 | Schneider |
| 5,074,847 A | 12/1991 | Greenwell et al. |

(56) References Cited

U.S. PATENT DOCUMENTS

| | | |
|---|---|---|
| D323,390 S | 1/1992 | Paine et al. |
| 5,084,026 A | 1/1992 | Shapiro |
| 5,098,048 A | 3/1992 | Chen |
| 5,098,399 A | 3/1992 | Tollini |
| 5,105,807 A | 4/1992 | Kahn et al. |
| 5,112,313 A | 5/1992 | Sallee |
| 5,116,324 A | 5/1992 | Brierley et al. |
| 5,120,320 A | 6/1992 | Fayngold |
| 5,135,506 A | 8/1992 | Gentelia et al. |
| 5,137,519 A | 8/1992 | Littrell et al. |
| 5,147,322 A | 9/1992 | Bowen et al. |
| 5,156,641 A | 10/1992 | White |
| 5,192,273 A | 3/1993 | Bierman |
| 5,192,274 A | 3/1993 | Bierman |
| 5,195,981 A | 3/1993 | Johnson |
| 5,215,532 A | 6/1993 | Atkinson |
| 5,226,892 A | 7/1993 | Boswell |
| 5,236,421 A | 8/1993 | Becher |
| 5,238,010 A | 8/1993 | Grabenkort et al. |
| 5,248,306 A | 9/1993 | Clark et al. |
| 5,263,943 A | 11/1993 | Vanderbrook |
| 5,266,401 A | 11/1993 | Tollini |
| 5,267,967 A | 12/1993 | Schneider |
| 5,279,578 A | 1/1994 | Cooke |
| 5,290,248 A | 3/1994 | Bierman et al. |
| 5,292,013 A | 3/1994 | Earl |
| 5,292,312 A | 3/1994 | Delk et al. |
| 5,304,146 A | 4/1994 | Johnson et al. |
| 5,306,243 A | 4/1994 | Bonaldo |
| D347,060 S | 5/1994 | Bierman |
| 5,308,337 A | 5/1994 | Bingisser |
| 5,314,411 A | 5/1994 | Bierman et al. |
| 5,322,097 A | 6/1994 | Wright |
| 5,328,487 A | 7/1994 | Starchevich |
| 5,334,186 A | 8/1994 | Alexander |
| 5,336,195 A | 8/1994 | Daneshvar |
| 5,338,308 A | 8/1994 | Wilk |
| 5,342,317 A | 8/1994 | Claywell |
| 5,344,406 A | 9/1994 | Spooner |
| 5,344,414 A | 9/1994 | Lopez et al. |
| 5,352,211 A | 10/1994 | Merskelly |
| 5,354,282 A | 10/1994 | Bierman |
| 5,356,379 A | 10/1994 | Vaillancourt |
| 5,356,391 A | 10/1994 | Stewart |
| 5,370,627 A | 12/1994 | Conway |
| 5,372,589 A | 12/1994 | Davis |
| 5,380,293 A | 1/1995 | Grant |
| 5,380,294 A | 1/1995 | Persson |
| 5,380,301 A | 1/1995 | Prichard et al. |
| 5,380,395 A | 1/1995 | Uchida |
| 5,382,239 A | 1/1995 | Orr et al. |
| 5,382,240 A | 1/1995 | Lam |
| 5,389,082 A | 2/1995 | Baugues et al. |
| 5,395,344 A | 3/1995 | Beisang, III et al. |
| 5,402,776 A | 4/1995 | Islava |
| 5,403,285 A | 4/1995 | Roberts |
| 5,413,120 A | 5/1995 | Grant |
| 5,413,562 A | 5/1995 | Swauger |
| D359,120 S | 6/1995 | Sallee et al. |
| 5,443,460 A | 8/1995 | Miklusek |
| 5,449,344 A | 9/1995 | Taylor et al. |
| 5,456,671 A | 10/1995 | Bierman |
| 5,468,231 A | 11/1995 | Newman et al. |
| 5,470,321 A | 11/1995 | Forster et al. |
| D364,922 S | 12/1995 | Bierman |
| 5,484,420 A | 1/1996 | Russo |
| 5,484,425 A | 1/1996 | Fischell et al. |
| 5,494,245 A | 2/1996 | Suzuki et al. |
| 5,496,282 A | 3/1996 | Militzer et al. |
| 5,496,283 A | 3/1996 | Alexander |
| 5,498,241 A | 3/1996 | Fabozzi |
| 5,499,976 A | 3/1996 | Dalton |
| 5,507,535 A | 4/1996 | McKamey et al. |
| 5,520,656 A | 5/1996 | Byrd |
| 5,522,803 A | 6/1996 | Teissen-Simony |
| 5,527,293 A | 6/1996 | Zamierowski |
| 5,531,695 A | 7/1996 | Swisher |
| 5,539,020 A | 7/1996 | Bracken et al. |
| 5,549,567 A | 8/1996 | Wolman |
| 5,551,421 A | 9/1996 | Noureldin et al. |
| D375,355 S | 11/1996 | Bierman |
| 5,577,516 A | 11/1996 | Schaeffer |
| 5,578,013 A | 11/1996 | Bierman |
| 5,593,395 A | 1/1997 | Martz |
| 5,605,546 A | 2/1997 | Wolzinger et al. |
| 5,620,427 A | 4/1997 | Werschmidt et al. |
| 5,626,565 A | 5/1997 | Landis et al. |
| 5,637,098 A | 6/1997 | Bierman |
| 5,643,217 A | 7/1997 | Dobkin |
| 5,664,581 A | 9/1997 | Ashley |
| 5,681,290 A | 10/1997 | Alexander |
| 5,685,859 A | 11/1997 | Kornerup |
| 5,686,096 A | 11/1997 | Khan et al. |
| 5,690,616 A | 11/1997 | Mogg |
| 5,690,617 A | 11/1997 | Wright |
| 5,693,032 A | 12/1997 | Bierman |
| 5,702,371 A | 12/1997 | Bierman |
| D389,911 S | 1/1998 | Bierman |
| 5,722,959 A | 3/1998 | Bierman |
| 5,728,053 A | 3/1998 | Calvert |
| 5,755,225 A | 5/1998 | Hutson |
| 5,776,106 A | 7/1998 | Matyas |
| 5,800,402 A | 9/1998 | Bierman |
| 5,800,410 A | 9/1998 | Gawreluk |
| 5,810,781 A | 9/1998 | Bierman |
| D399,954 S | 10/1998 | Bierman |
| 5,827,230 A | 10/1998 | Bierman |
| 5,827,239 A | 10/1998 | Dillon et al. |
| 5,833,666 A | 11/1998 | Davis et al. |
| 5,833,667 A | 11/1998 | Bierman |
| 5,846,255 A | 12/1998 | Casey |
| 5,855,591 A | 1/1999 | Bierman |
| 5,885,251 A | 3/1999 | Luther |
| 5,885,254 A | 3/1999 | Matyas |
| 5,897,519 A | 4/1999 | Shesol et al. |
| 5,911,707 A | 6/1999 | Wolvek et al. |
| 5,916,199 A | 6/1999 | Miles |
| 5,922,470 A | 7/1999 | Bracken et al. |
| 5,944,696 A | 8/1999 | Bayless et al. |
| 5,947,931 A | 9/1999 | Bierman |
| 6,015,119 A | 1/2000 | Starchevich |
| 6,050,934 A | 4/2000 | Mikhail et al. |
| 6,054,523 A | 4/2000 | Braun et al. |
| D425,619 S | 5/2000 | Bierman |
| 6,058,574 A | 5/2000 | Facey et al. |
| 6,067,985 A | 5/2000 | Islava |
| 6,099,509 A | 8/2000 | Brown, Jr. et al. |
| 6,113,577 A | 9/2000 | Hakky et al. |
| 6,131,575 A | 10/2000 | Lenker et al. |
| 6,132,398 A | 10/2000 | Bierman |
| 6,132,399 A | 10/2000 | Shultz |
| D433,503 S | 11/2000 | Powers et al. |
| 6,206,897 B1 | 3/2001 | Jamiolkowski et al. |
| 6,213,979 B1 | 4/2001 | Bierman |
| 6,213,996 B1 | 4/2001 | Jepson et al. |
| 6,216,885 B1 | 4/2001 | Guillaume |
| 6,224,571 B1 | 5/2001 | Bierman |
| 6,228,064 B1 | 5/2001 | Abita et al. |
| 6,231,547 B1 | 5/2001 | O'Hara |
| 6,231,548 B1 | 5/2001 | Bassett |
| 6,234,465 B1 | 5/2001 | Sutton, Jr. |
| 6,258,066 B1 | 7/2001 | Urich |
| 6,273,873 B1 | 8/2001 | Fleischer |
| 6,283,945 B1 | 9/2001 | Bierman |
| 6,287,281 B1 | 9/2001 | Nishtala et al. |
| 6,290,676 B1 | 9/2001 | Bierman |
| 6,332,874 B1 | 12/2001 | Eliasen et al. |
| 6,361,523 B1 | 3/2002 | Bierman |
| 6,375,639 B1 | 4/2002 | Duplessie et al. |
| 6,387,075 B1 | 5/2002 | Stivland et al. |
| 6,387,076 B1 | 5/2002 | Landuyt |
| 6,413,240 B1 | 7/2002 | Bierman et al. |
| 6,428,515 B1 | 8/2002 | Bierman et al. |
| 6,428,516 B1 | 8/2002 | Bierman |

(56) References Cited

U.S. PATENT DOCUMENTS

| | | |
|---|---|---|
| 6,436,073 B1 | 8/2002 | Von Teichert |
| 6,447,485 B2 | 9/2002 | Bierman |
| 6,447,486 B1 | 9/2002 | Tollini |
| 6,471,676 B1 | 10/2002 | DeLegge et al. |
| 6,482,183 B1 | 11/2002 | Pausch et al. |
| 6,488,664 B1 | 12/2002 | Solomon et al. |
| 6,491,664 B2 | 12/2002 | Bierman |
| 6,500,154 B1 | 12/2002 | Hakky et al. |
| D469,530 S | 1/2003 | Gomez |
| 6,517,522 B1 | 2/2003 | Bell et al. |
| 6,551,285 B1 | 4/2003 | Bierman |
| 6,572,588 B1 | 6/2003 | Bierman et al. |
| 6,582,403 B1 | 6/2003 | Bierman et al. |
| 6,596,402 B2 | 7/2003 | Soerens et al. |
| 6,616,635 B1 | 9/2003 | Bell et al. |
| 6,626,890 B2 | 9/2003 | Nguyen et al. |
| 6,652,487 B1 | 11/2003 | Cook |
| 6,663,600 B2 | 12/2003 | Bierman et al. |
| 6,673,046 B2 | 1/2004 | Bierman et al. |
| 6,689,104 B2 | 2/2004 | Bierman |
| 6,703,120 B1 | 3/2004 | Ko et al. |
| 6,770,055 B2 | 8/2004 | Bierman et al. |
| 6,786,892 B2 | 9/2004 | Bierman |
| 6,809,230 B2 | 10/2004 | Hancock et al. |
| 6,827,705 B2 | 12/2004 | Bierman |
| 6,827,706 B2 | 12/2004 | Tollini |
| 6,827,707 B2 | 12/2004 | Wright et al. |
| 6,834,652 B2 | 12/2004 | Altman |
| 6,837,875 B1 | 1/2005 | Bierman |
| 6,866,652 B2 | 3/2005 | Bierman |
| 6,951,550 B2 | 10/2005 | Bierman |
| 6,972,003 B2 | 12/2005 | Bierman et al. |
| 6,979,320 B2 | 12/2005 | Bierman |
| 6,981,969 B2 | 1/2006 | Chavez et al. |
| 7,014,627 B2 | 3/2006 | Bierman |
| 7,018,362 B2 | 3/2006 | Bierman et al. |
| 7,070,580 B2 | 7/2006 | Nielsen |
| 7,090,660 B2 | 8/2006 | Roberts et al. |
| 7,115,321 B2 | 10/2006 | Soerens et al. |
| 7,153,291 B2 | 12/2006 | Bierman |
| 7,201,739 B2 | 4/2007 | Walborn |
| 7,214,215 B2 | 5/2007 | Heinzerling et al. |
| 7,223,256 B2 | 5/2007 | Bierman |
| 7,250,880 B2 | 7/2007 | Hurrell et al. |
| 7,354,421 B2 | 4/2008 | Bierman |
| 7,413,561 B2 | 8/2008 | Raulerson et al. |
| 7,491,190 B2 | 2/2009 | Bierman et al. |
| 7,520,870 B2 | 4/2009 | Bierman |
| 7,524,307 B2 | 4/2009 | Davis et al. |
| 7,566,325 B2 | 7/2009 | Lim et al. |
| 7,637,894 B2 | 12/2009 | Fleischer |
| 7,651,479 B2 | 1/2010 | Bierman |
| 7,744,572 B2 | 6/2010 | Bierman |
| 7,776,017 B2 | 8/2010 | Ponzi et al. |
| 7,799,001 B2 | 9/2010 | Bierman |
| 7,887,515 B2 | 2/2011 | Bierman |
| 7,967,792 B2 | 6/2011 | Bierman |
| 7,974,681 B2 | 7/2011 | Wallace et al. |
| 8,100,862 B2 | 1/2012 | Bierman |
| 8,105,290 B2 | 1/2012 | Wright et al. |
| 8,900,196 B2 | 12/2014 | Andino |
| 2001/0011164 A1 | 8/2001 | Bierman |
| 2002/0133121 A1 | 9/2002 | Bierman |
| 2002/0161332 A1 | 10/2002 | Ramey |
| 2002/0165494 A1 | 11/2002 | Bierman et al. |
| 2002/0188255 A1 | 12/2002 | Bierman et al. |
| 2003/0055382 A1 | 3/2003 | Schaeffer |
| 2004/0111067 A1 | 6/2004 | Kirchhofer |
| 2004/0170089 A1 | 9/2004 | Rund |
| 2004/0204685 A1 | 10/2004 | Wright et al. |
| 2004/0240324 A1 | 12/2004 | Isbitsky et al. |
| 2005/0038453 A1 | 2/2005 | Raulerson |
| 2005/0075610 A1 | 4/2005 | Bierman |
| 2005/0107738 A1 | 5/2005 | Slater et al. |
| 2005/0192539 A1 | 9/2005 | Bierman et al. |
| 2005/0215953 A1 | 9/2005 | Rossen |
| 2005/0251157 A1 | 11/2005 | Saadat et al. |
| 2005/0282977 A1 | 12/2005 | Stempel et al. |
| 2006/0025723 A1 | 2/2006 | Ballarini |
| 2006/0052755 A1 | 3/2006 | Lim et al. |
| 2006/0058789 A1 | 3/2006 | Kim et al. |
| 2006/0089600 A1 | 4/2006 | Bierman et al. |
| 2006/0094985 A1 | 5/2006 | Aceti et al. |
| 2006/0135944 A1 | 6/2006 | Bierman |
| 2006/0161087 A1 | 7/2006 | Carter et al. |
| 2006/0184129 A1 | 8/2006 | Bierman |
| 2006/0217669 A1 | 9/2006 | Botha |
| 2006/0247574 A1 | 11/2006 | Maule et al. |
| 2006/0247577 A1 | 11/2006 | Wright |
| 2006/0247661 A1 | 11/2006 | Richards et al. |
| 2006/0270995 A1 | 11/2006 | Bierman |
| 2006/0289011 A1 | 12/2006 | Helsel |
| 2007/0032561 A1 | 2/2007 | Lin et al. |
| 2007/0043385 A1 | 2/2007 | Nobles et al. |
| 2007/0060890 A1 | 3/2007 | Cuppy |
| 2007/0149930 A1 | 6/2007 | Bierman |
| 2007/0173768 A2 | 7/2007 | Bierman |
| 2007/0249980 A1 | 10/2007 | Carrez et al. |
| 2007/0276332 A1 | 11/2007 | Bierman |
| 2007/0276333 A1 | 11/2007 | Bierman |
| 2008/0027392 A1 | 1/2008 | Bierman |
| 2008/0249476 A1 | 10/2008 | Bierman et al. |
| 2009/0043260 A1 | 2/2009 | Bierman |
| 2009/0254040 A1 | 10/2009 | Bierman et al. |
| 2009/0299294 A1 | 12/2009 | Pinkus |
| 2009/0306603 A1 | 12/2009 | Bierman et al. |
| 2010/0179482 A1 | 7/2010 | Wright et al. |
| 2010/0179483 A1 | 7/2010 | Wright et al. |
| 2011/0178467 A1 | 7/2011 | Bierman et al. |
| 2011/0264050 A1 | 10/2011 | Henry et al. |
| 2011/0282291 A1 | 11/2011 | Ciccone |
| 2012/0041378 A1 | 2/2012 | Bierman |
| 2013/0079723 A1 | 3/2013 | Andino et al. |

FOREIGN PATENT DOCUMENTS

| | | |
|---|---|---|
| DE | 2341297 A1 | 4/1975 |
| EP | 0064284 A2 | 11/1982 |
| EP | 0114677 A2 | 8/1984 |
| EP | 0169704 A1 | 1/1986 |
| EP | 0247590 A2 | 12/1987 |
| EP | 0263789 A1 | 4/1988 |
| EP | 0356683 A1 | 3/1990 |
| EP | 0367549 A2 | 5/1990 |
| EP | 0720836 A2 | 7/1996 |
| EP | 0931560 A1 | 7/1999 |
| FR | 2381529 A1 | 9/1978 |
| FR | 2598625 A1 | 11/1987 |
| GB | 2063679 A | 6/1981 |
| GB | 2178811 A | 2/1987 |
| GB | 2211417 A | 7/1989 |
| GB | 2086466 A | 5/1992 |
| GB | 2472268 A | 2/2011 |
| JP | 62201159 A | 9/1987 |
| JP | 63501477 | 6/1988 |
| JP | 01308572 | 12/1989 |
| WO | 8001458 A1 | 7/1980 |
| WO | 90/04991 A1 | 5/1990 |
| WO | 9005559 A1 | 5/1990 |
| WO | 9116939 A1 | 11/1991 |
| WO | 9203070 A1 | 3/1992 |
| WO | 9203923 A1 | 3/1992 |
| WO | 9219309 A1 | 11/1992 |
| WO | 9219314 A1 | 11/1992 |
| WO | 9412231 A1 | 6/1994 |
| WO | 9421319 A1 | 9/1994 |
| WO | 9610435 A1 | 4/1996 |
| WO | 9715337 A1 | 5/1997 |
| WO | 9715342 A1 | 5/1997 |
| WO | 9853872 A1 | 12/1998 |
| WO | 9955409 A1 | 11/1999 |
| WO | 2004016309 A2 | 2/2004 |
| WO | 2005105194 A1 | 11/2005 |
| WO | 2007117655 A2 | 10/2007 |

(56) References Cited

FOREIGN PATENT DOCUMENTS

| WO | 2008051810 A2 | 5/2008 |
|---|---|---|
| WO | 2008151047 A1 | 12/2008 |
| WO | 2009055739 A1 | 4/2009 |
| WO | 2010102153 A1 | 9/2010 |

OTHER PUBLICATIONS

ARROW® "Snap-Lock" Catheter/Syringe Adapter, 1 page, K-05500-103A (Jan. 1990).
PCT/US2010/051659 filed Jun. 10, 2010 International Search Report dated Dec. 3, 2010.
PCT/US2010/051706 filed Jun. 10, 2010 International Search Report and Written Opinion dated Dec. 2, 2010.
Search Result, Percufix® Catheter Cuff Kit, downloaded from the Internet on Aug. 15, 2001.
U.S. Appl. No. 13/498,117, filed Dec. 10, 2012 Final Office Action dated Nov. 2, 2015.
U.S. Appl. No. 13/498,117, filed Dec. 10, 2012 Non-Final Office Action dated Jul. 22, 2015.
U.S. Appl. No. 13/498,118, filed Jul. 2, 2012 Final Office Action dated Oct. 22, 2015.
International Search Report and Written Opinion of PCT/US12/34533, mailed on Aug. 10, 2012.
CA 2775570 filed Mar. 27, 2012 Office Action dated Aug. 8, 2016.
CA 2776239 filed Mar. 29, 2012 Office Action dated Jul. 15, 2016.

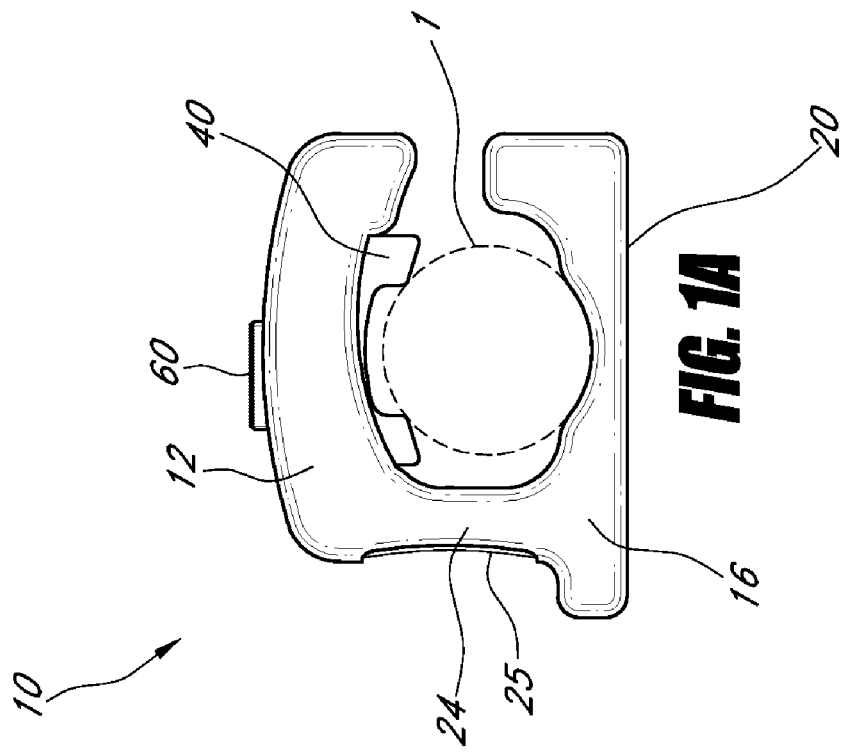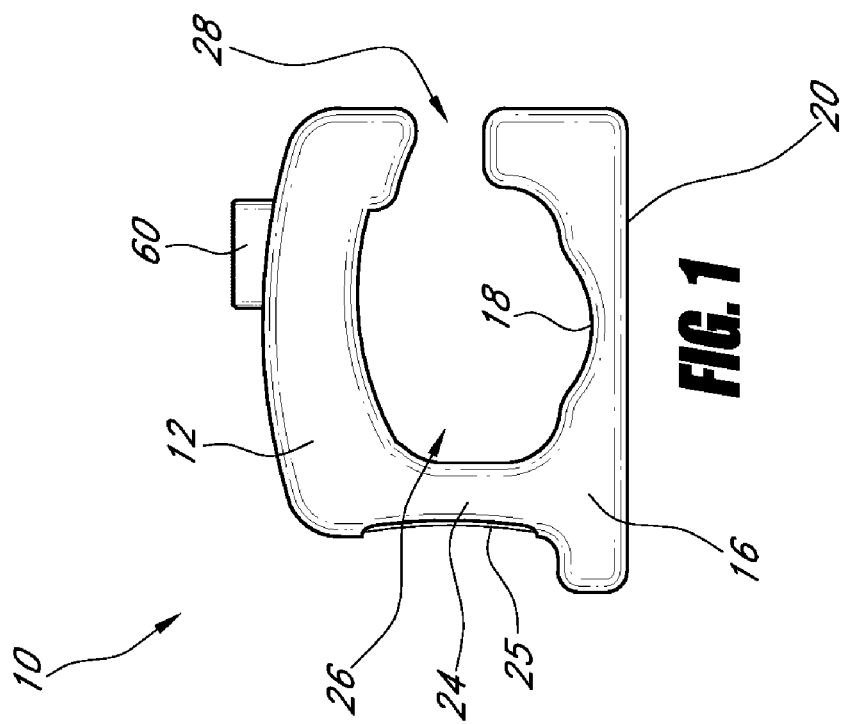

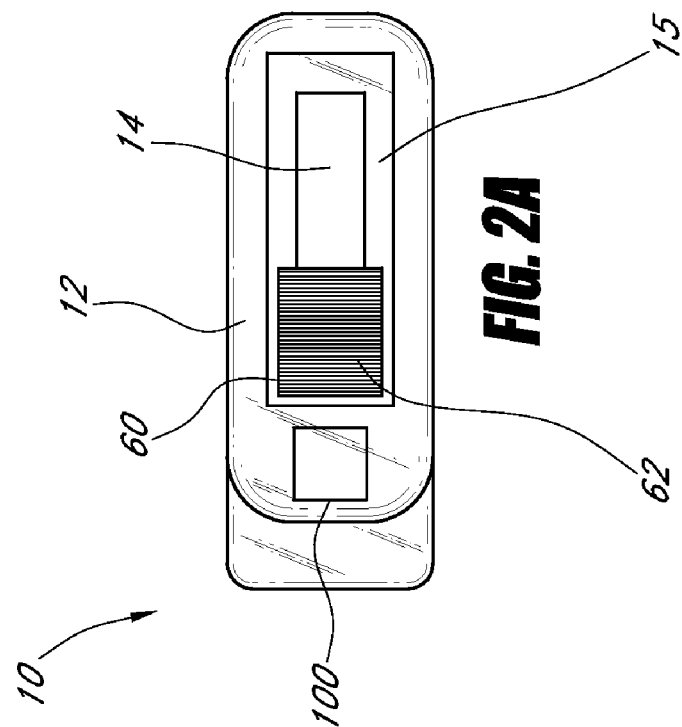
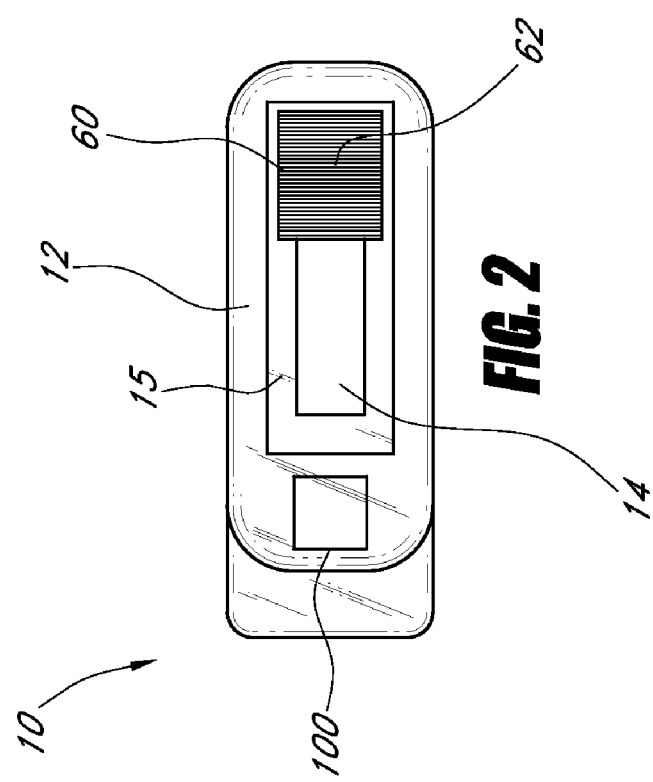

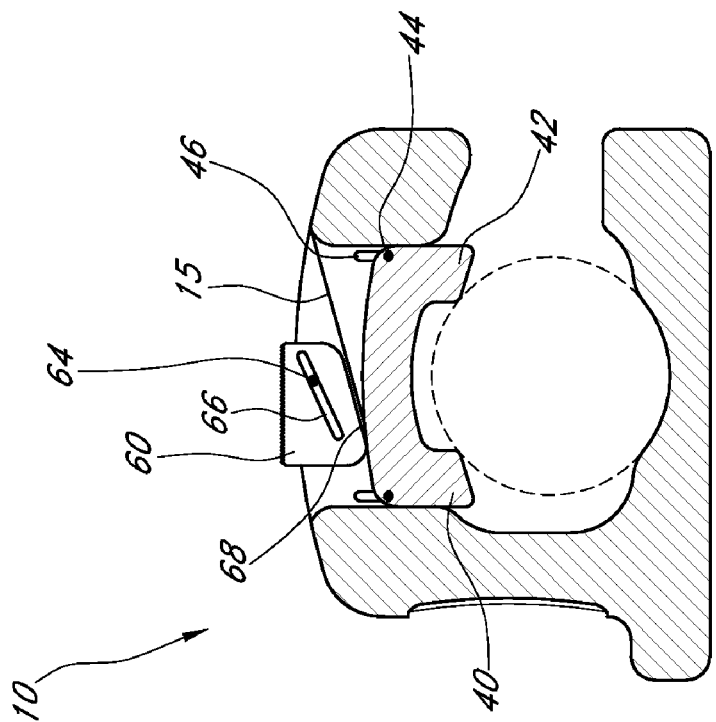
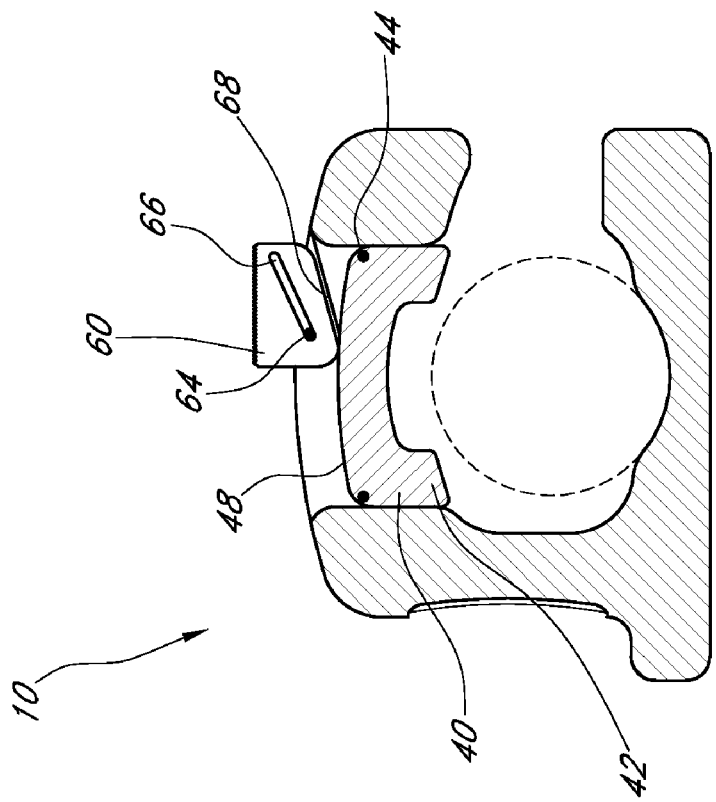

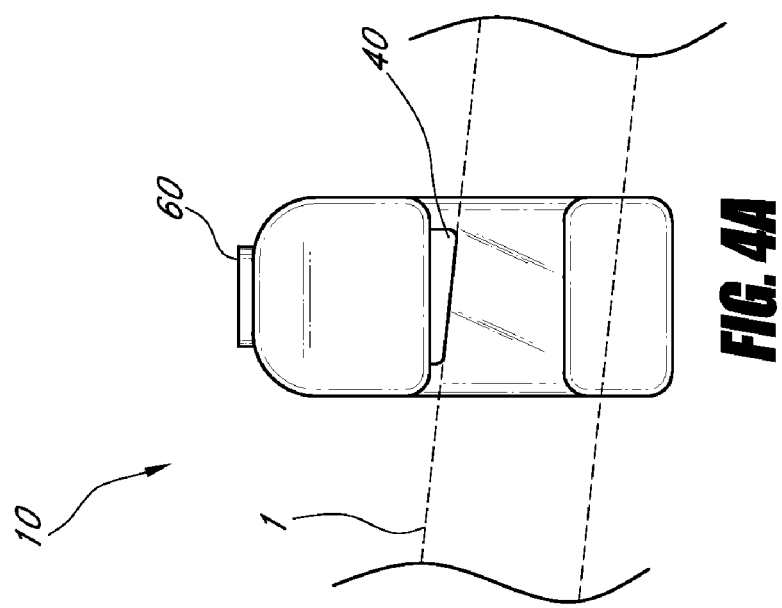
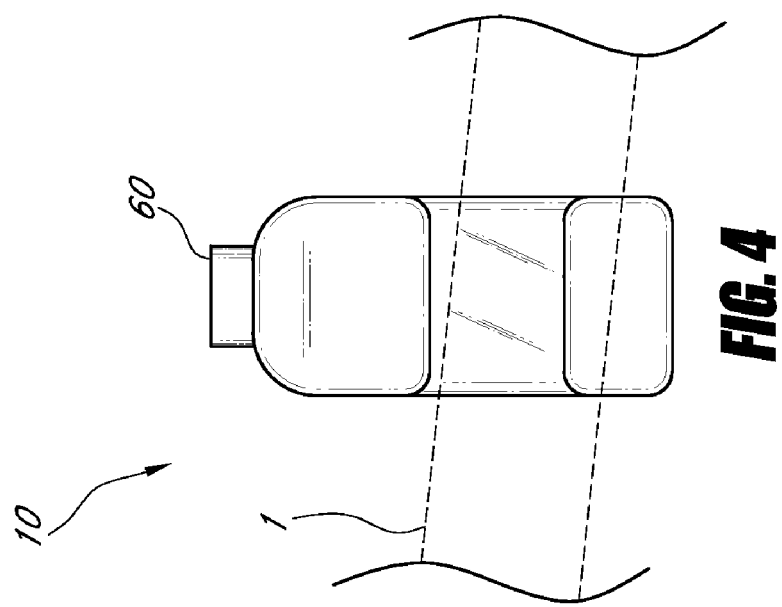

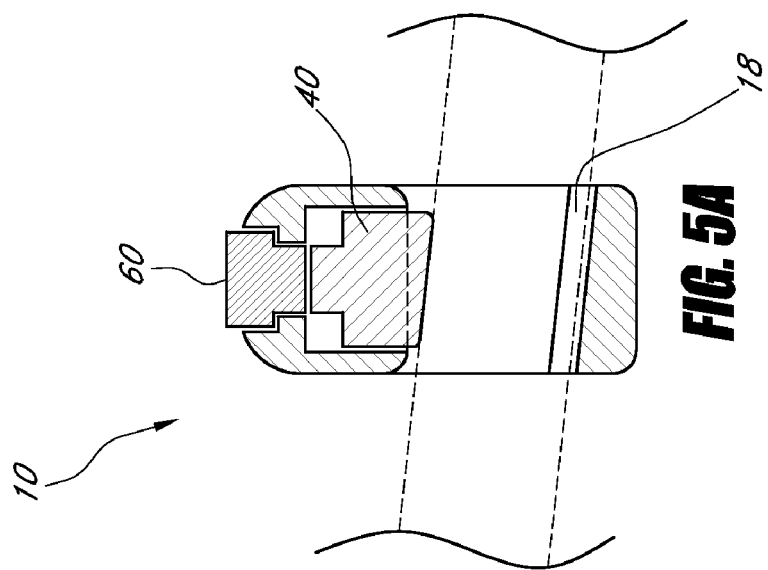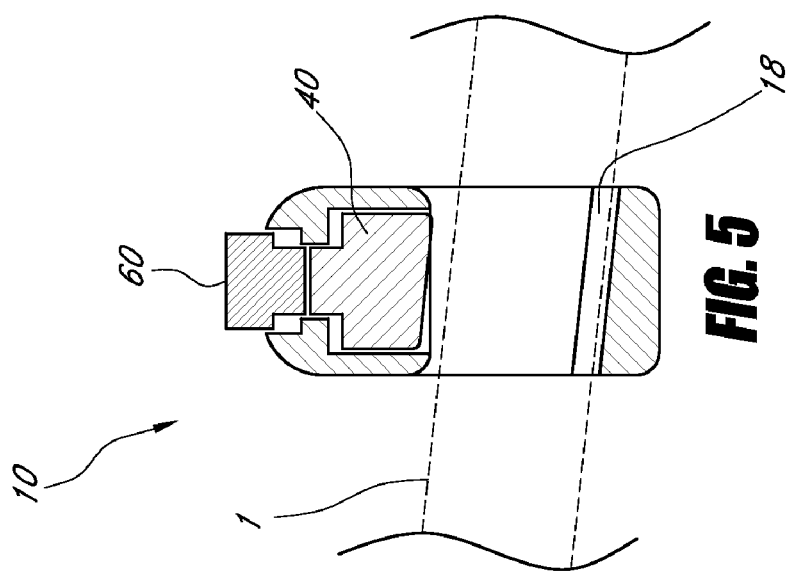

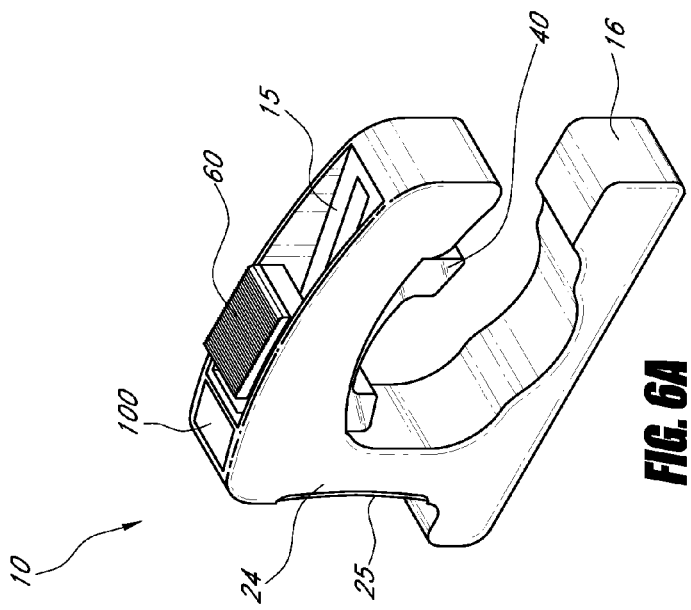
FIG. 6A
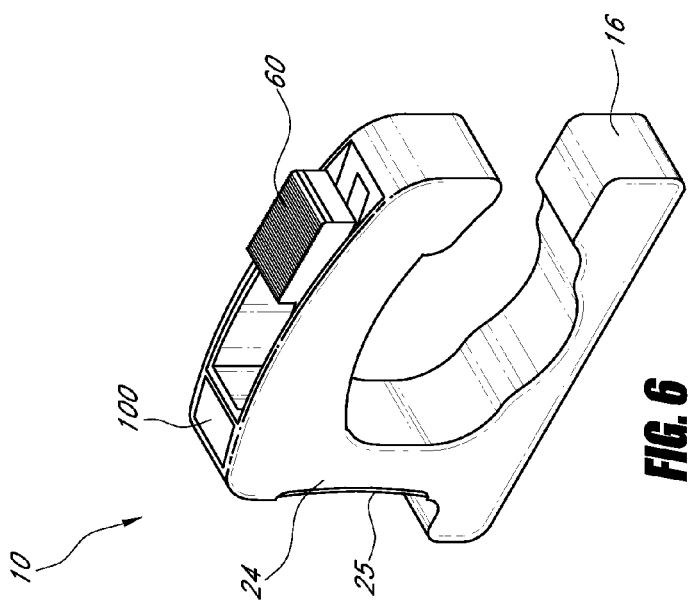
FIG. 6
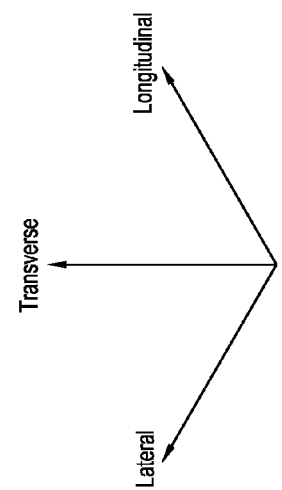

ANCHORING SYSTEM

PRIORITY INFORMATION

This application is a continuation of U.S. patent application Ser. No. 13/452,291, filed Apr. 20, 2012, now U.S. Pat. No. 8,900,196, which claims the priority benefit under 35 U.S.C. §119(e) to U.S. Provisional Application No. 61/478,027, filed Apr. 21, 2011 and titled ANCHORING SYSTEM, the entirety of each of which is hereby expressly incorporated by reference herein.

BACKGROUND

1. Field

The present invention relates to anchoring systems. For example, the present invention may relate to a system for securing a medical article to a patient to inhibit movement or migration of the medical article relative to a patient.

2. Description of the Related Art

Hospitalized patients often have limited mobility due either to their condition or to doctor's orders. Such patients must lie in bed and not move about their hospital room, even to urinate. As such, various devices are used with bed-confined patient to drain various bodily fluids, or insert various forms of medicine or other substances into the body, as needed.

Often, a healthcare provider may secure tubes for draining and inserting such fluids to a patient using tape. For example, a healthcare provider may place long pieces of tape across the distal end of the tube in a crisscross pattern to secure the tube distal end to the inner thigh of the patient. This securement inhibits disconnection between the tube and the patient, as well as prevents the tube from snagging on the bed rail or other objects.

Taped connections, however, often collect contaminants and dirt. Normal protocol therefore requires periodic tape changes in order to inhibit bacteria and germ growth at the securement site. Frequent tape changes though lead to another problem: excoriation of the patient's skin. In addition, valuable time is spent applying and reapplying the tape to secure the catheter. And health care providers often remove their gloves when taping because most find the taping procedure difficult and cumbersome when wearing gloves. Not only does this further lengthen the procedure, but it also subjects the healthcare provider to possible infection.

SUMMARY

Embodiments can include several features for an anchoring system useful for the securement of a medical article to a patient's body. Without limiting the scope, certain prominent features will be discussed briefly. After considering this discussion, and particularly after reading the Detailed Description of Certain Preferred Embodiments section below in combination with this section, one will understand how some features and aspects of these embodiments provide several advantages over prior securement devices.

For example, in one embodiment a retainer secures a medical article to a patient. The retainer can include a first member defining at least a portion of a channel and having a receptacle. The channel can include a longitudinal axis and be configured to receive at least a portion of a medical article. The retainer further includes a second member. At least a portion of the second member is movably retained within at least a portion of the receptacle so as to move between a first position and a second position. The second member contacts at least a part of the received portion of the medical article at least when in the second position so as to inhibit longitudinal movement of the medical article through the channel.

In another embodiment, a securement device secures at least a portion of a medical article. The device includes a first arm having a guideway extending through the first arm and an engaging piece movably disposed within at least a portion of the guideway so as to at least move through the guideway and towards the medical article. The first arm further includes an actuator movably disposed within at least a portion of the guideway and coupled to the engaging piece so that movement of the actuator moves the engaging piece. The device further includes a second arm having a surface facing the first arm. The surface is configured to locate the medical article to be contacted by the engaging piece. The device further includes a connecting portion operatively connecting the first and second arms.

In another embodiment, a securement device secures at least a portion of a medical article. The device includes a first portion having a first contact surface for receiving a medical article and a second portion operatively fixed relative to the first portion and having a second contact surface. The second contact surface is disposed so as to oppose the first contact surface and define a receiving space therebetween. The device further includes a member movably coupled to the second portion so as to move between a first position and a second position. The member is closer to the first contact surface when in the second position than when in the first position. At least a part of the member extends into the receiving space at least when in the second position so as to contact at least a portion of the received medical article and inhibit longitudinal movement of the medical article through the receiving space.

In another embodiment, a method secures a medical article relative to a patient. The method includes providing a retainer forming a channel and having a first opening, a second opening, and an engaging piece. The first opening is in a side of the retainer. The engaging piece is movably disposed within at least a portion of the second opening. The method further includes passing at least a portion of the medical article through the first opening and into the channel so that at least a portion of the medical article is aligned with the second opening and moving the engaging piece through the second opening in a direction towards the portion of the medical article and into the channel. The method further includes contacting the medical article with the engaging piece so as to inhibit longitudinal movement of the medical article through the channel and securing the retainer relative to the patient.

BRIEF DESCRIPTION OF THE DRAWINGS

These and other features, aspects, and advantages of the anchoring system disclosed herein are described below with reference to the drawings of preferred embodiments, which are intended to illustrate and not to limit the invention. Additionally, from figure to figure, the same reference numerals have been used to designate the same components of an illustrated embodiment. The following is a brief description of each of the drawings.

FIG. 1 is a front view of one embodiment of a securement device in an unsecured position according to a preferred embodiment of the present invention;

FIG. 1A is a front view of the securement device of FIG. 1, in a secured position;

FIG. 2 is a top view of the securement device of FIG. 1, in the position depicted in FIG. 1;

FIG. 2A is a top view of the securement device of FIG. 1, in the position depicted in FIG. 1A;

FIG. 3 is a cross-sectional view of the securement device of FIG. 1, in the position depicted in FIG. 1;

FIG. 3A is a cross-sectional view of the securement device of FIG. 1, in the position depicted in FIG. 1A;

FIG. 4 is a side view of the securement device of FIG. 1, in the position depicted in FIG. 1;

FIG. 4A is a side view of the securement device of FIG. 1, in the position depicted in FIG. 1A;

FIG. 5 is a side cross-sectional view of the securement device of FIG. 1, in the position depicted in FIG. 1;

FIG. 5A is a side cross-sectional view of the securement device of FIG. 1, in the position depicted in FIG. 1A;

FIG. 6 is a perspective view of the securement device of FIG. 1, in the position depicted in FIG. 1; and FIG. 6A is a perspective view of the securement device of FIG. 1, in the position depicted in FIG. 1A.

DETAILED DESCRIPTION OF CERTAIN PREFERRED EMBODIMENTS

Certain preferred embodiments are described herein relating to the securement of a medical device to a patient. However, the principles of the inventions described herein are not limited to medical devices, nor to the securement of articles to a patient. For example, in some embodiments the inventions described herein can be used to secure electrical wires, ventilation conduits, or other articles to an inanimate body. Thus, the particular embodiments described herein and the context in which they are described should not be considered to limit the scope of the inventions disclosed herein.

Figure 7A:
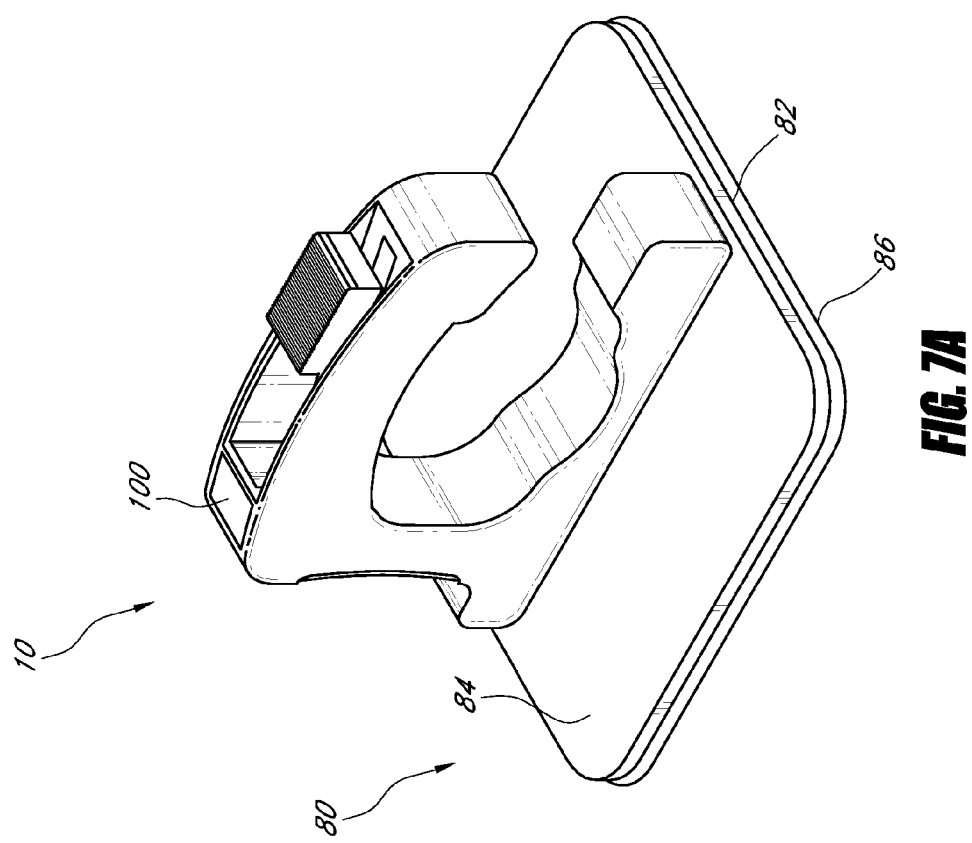
FIG. 7A is a perspective view of the securement device of FIG. 1 mounted to the anchor pad of FIG. 7.
Figure 7:
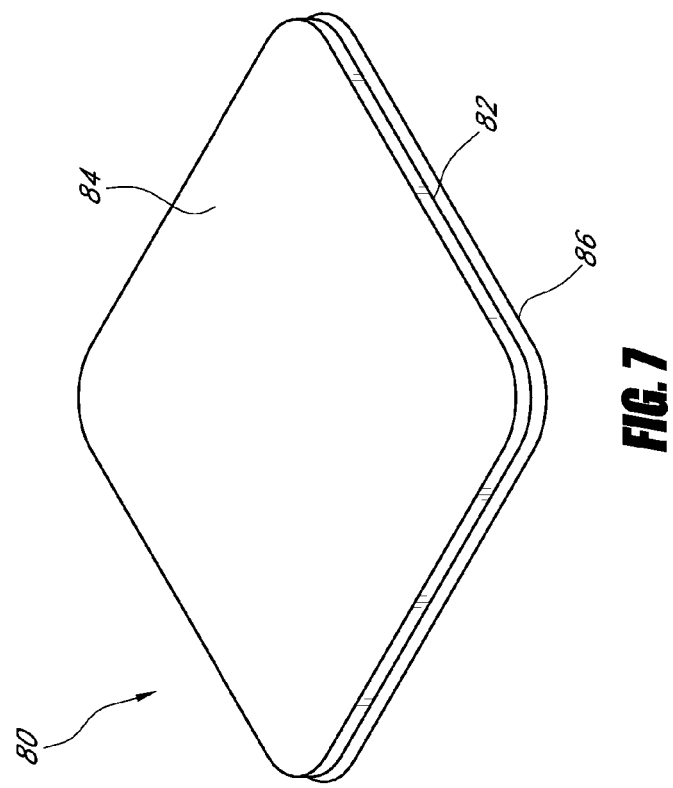
FIG. 7 is a perspective view of an anchor pad.

Generally, the Figures are provided in pairs, each showing a distinct view of a securement device 10 in two positions, described herein as an unsecured position (e.g., FIG. 1) and a secured position (e.g., FIG. 1A), with the exception of FIGS. 7 and 7A. However, in other embodiments additional positions may be provided. For example, as depicted in FIGS. 1 and 1A, the securement device 10 is configured to secure a medical article 1 of a particular size. However, in other embodiments a similar securement device may be configured to secure two or more articles of different sizes, requiring similarly different positions. Further, in some embodiments a securement device may be configured to secure more than one device, and thus may require distinct positions to secure, for example, zero, one, or two of two total articles.

Further, as best shown by comparing FIGS. 1A and 4-5A, the secured article 1 is depicted as having a cylindrical shape. However, it will be understood that other shapes are possible, such as a polygonal columnar shape, a conical shape, a cubic shape, a forked shape, or the like. In some embodiments the article 1 is a medical article such as a tube for a catheter. Exemplary secured articles include catheters and catheter hubs of various design, including central venous catheters, peripherally inserted central catheters, hemodialysis catheters, Foley catheters, as well as other designs of catheter hubs and catheter adaptors. Other medical articles may include surgical drainage tubes, feeding tubes, chest tubes, nasogastric tubes, rectal drains, external ventricular drains, chest tubes, any other sort of fluid supply or medical lines, connector fittings, and scopes, as well as electrical wires or cables connected to external or implanted electronic devices or sensors. The medical articles can each be a single medical article or a combination of medical articles.

As shown, for example, in FIGS. 1 and 1A, the securement device 10 can comprise a generally C-shape structure. The securement device 10 can include a first arm 12, a second arm 16, and a connecting portion 24. The first arm 12 can be an upper arm and, as discussed further below, can house an actuator 60 and an engagement piece 40. The connecting portion 24 can serve to connect the first arm 12 and the second arm 16. Further, the connecting portion 24 can comprise a curved portion 25 providing an improved ergonomic grip. Finally, the second arm 16 can be a lower arm.

The second arm 16 can additionally comprise a groove 18. The groove 18 can be provided in a longitudinal direction to receive and align the article 1 passing longitudinally through the securement device 10. In some embodiments, the groove 18 can further be shaped to generally match a portion(s) of the article 1 so as to improve the fit between these features. The second arm 16 can further comprise an external surface 20 depicted as a lower surface. Generally, this lower surface 20 of the securement device 10 can be configured to engage with a surface on which the securement device 10 is configured to rest. For example, in some embodiments the securement device 10 may be configured to be applied to a patient via an anchor pad 80, as depicted in FIGS. 7 and 7A, or applied directly to the patient. For example, the lower surface 20 can comprise a bio-compatible adhesive or be configured to attach to another article secured to the patient. Further, in some embodiments the lower surface 20 may be shaped to improve securement, such as with a curved shape to match a curved surface.

For embodiments that include an anchor pad 80, the size and shape of the anchor pad can vary depending on where the anchor pad is intended to be positioned on a patient. For example, in some embodiments the securement device 10 is intended for placement on a patient's hand and in other embodiments, the securement device 10 is intended for placement on a different part of a patient, for example, a patient's back. The anchor pad 80 may be any size or shape that allows attachment of the anchor pad to a patient's skin and that is configured to support at least the securement device 10. The anchor pad 80 can be configured to support more than one securement device 10. For example, as depicted in FIGS. 7 and 7A, the anchor pad 80 has a square shape. Further, in FIGS. 7 and 7A, the achor pad 80 is shown as holding only one securement device 10, but has a size sufficient to hold more than one securement device.

The anchor pad 80 has a lower adhesive surface 82 for adhering to the skin of a patient and an upper surface 84. The upper surface is configured to support at least the securement device 10, as described above. In combination, the lower adhesive surface 82, the upper surface 84, and possibly one or more intermediate layers may comprise a laminate structure. A suitable laminate that comprises a foam or woven material with an adhesive layer is available commercially from Avery Dennison of Painsville, Ohio. The anchor pad 10 may be configured as a flexible structure configured to conform to the surface of a patient's skin.

The lower adhesive surface 82 or layer may be a medical-grade adhesive and can be either diaphoretic or non-diaphoretic, depending upon the particular application. The lower adhesive surface 82 may have additional types of medical adhesives laminated thereto. In some embodiments, the lower adhesive layer 82 comprises an anti-bacterial or antimicrobial material. For example, the lower adhesive layer 82 may comprise one or more oligodynamic metal salts or oxides, or a combination of salts and oxides. In some embodiments, the lower adhesive layer 82 comprises a silver material, for example a silver salt, colloid, or complex. The adhesive layer 82 may be a solid layer or may be configured as an intermittent layer such as in a pattern of spots or strips. The lower adhesive layer 82 can be applied to the anchor pad 10 during manufacture, and may be further covered with a release liner 86.

The upper surface 84 may comprise a foam (e.g., closed-cell polyethylene foam) or woven material (e.g., tricot) layer. A surface of the foam or woven material layer can constitute the upper surface 84 of the anchor pad 10. In the alternative, the upper surface 84 may comprise an upper paper or other nonwoven cloth layer, and an inner foam layer may be placed between the upper surface and lower adhesive layer.

A removable release liner 86 may cover the lower adhesive layer 82 before use. The release liner 86 may resist tearing and be divided into a plurality of pieces to assist removal of the release liner and ease attachment of the anchor pad 80 to a patient's skin. The release liner 86 may be divided into two adjacent pieces. The liner 86 may be made of a paper, plastic, polyester, or similar material. For example, the release liner 86 may comprise a material made of polycoated, siliconized paper, or another suitable material such as high density polyethylene, polypropylene, polyolefin, or silicon coated paper.

The securement device 10 can form a central cavity or channel 26. In the depicted embodiment, the central cavity 26 is substantially defined by the first arm 12, second arm 16, and the connecting portion 24, although in other embodiments it can be substantially formed or defined by other sets of features. Further, as depicted, the central cavity 26 can extend in a longitudinal direction and include an opening 28. The opening 28 may face any direction. Thus, in the depicted embodiment there is a plurality of techniques for inserting the article 1 into the central cavity 26. In one method, the article 1 is inserted longitudinally, through the cavity 26, independent of the opening 28. However, this method might not be possible with some articles, such as articles that have ends sufficiently large to not fit through the central cavity 26, even though a middle portion of the article can fit. In another method, the article 1 is inserted laterally, through the opening 28. Inserting the article 1 laterally through the opening 28 can be accomplished even if ends of the article might not fit in the channel or central cavity 26.

Inserting the article 1 laterally through the opening 28 may provide certain advantages with long and flexible articles, such as medical tubing. For example, a long article 1, even if it fits, might dissuade insertion longitudinally (independent of the opening 28) because this may require extensive threading to secure the article at a desired location potentially far from an end of the article.

Use of a flexible article during insertion laterally through the opening 28 can also provide for some additional securement independent of other mechanisms discussed herein. For example, if the size of the opening 28 is smaller than the natural size of the article 1, the article 1 may need to be flexed or squeezed to fit through the opening 28 and into the cavity 26. Similarly, the article 1 would need to be flexed or squeezed to be removed from the cavity 26 through the opening 28. The forces necessary to allow such travel can provide some securement of the article 1 within the cavity 26.

As best depicted in FIGS. 3, 3A, the article 1 is at least partially secured within the central cavity 26 of the securement device 10 by a movable engagement piece 40. For example, as depicted the engagement piece 40 can include two projecting ends 42 configured to engage the constrained article 1. In some embodiment, the projecting ends 42 can comprise a gripping surface that may comprise an adhesive, one or more ridges or bumps, or other features that may improve grip on the constrained article 1. In this embodiment, the engagement piece 40 is provided within the first arm 12, although in other embodiments it can be provided elsewhere in the device 10. For example, the engagement piece 40 could be disposed in the connecting portion 24.

The engagement piece 40 moves between locked and unlocked positions. For example, the engagement piece 40 can be partially constrained so it does not move in the lateral and longitudinal directions while being movable in the transverse direction. When in the locked position, a secured article 1 is prevented from moving in at least one direction by way of its engagement with the engagement piece 40. In at least one embodiment, the engagement piece 40 primarily moves in a radial direction towards and away from the cavity 26 while being constrained from moving in the lateral and longitudinal directions. For example, the engagement piece 40 may slide in a transverse direction towards and away from a central axis of the cavity 26 while being constrained from moving in the longitudinal and lateral directions.

A portion of the engagement piece 40 may slide within one or more slots or grooves in the device 10. These slots or grooves could extend in a transverse direction and be disposed in the first arm 12. The portion of the engagement piece 40 which slides within the slot or groove could have the shape of a ridge, protrusion, pin, projection, or other like structure. The portion could be a separate structure attached to the engagement piece 40 or an integral portion of the piece. For example, the portion could be a pin projecting from a surface of the engagement piece 40. A tongue and groove arrangement could be employed between the engagement piece 40 and the device 10.

Alternatively or in addition, the entire engagement piece 40 may slide within a passage that has a cross-section that generally matches the cross-section of the engagement piece 40 without the need for a slot or groove.

Further, in the depicted embodiment the engagement piece 40 moves in a downward transverse direction into the cavity 26, although in other embodiments the motion can be in other directions. The direction of the motion for the illustrated embodiment is at least partially defined by one or more pins 44. The pins 44 can extend in the longitudinal direction from the engagement piece 40, and correspond with grooves 46 formed within the body of the first arm 12. Thus, the pins 44 can slide within the pin grooves 46 to constrain the motion of the engagement piece 40. As the grooves 46 are depicted as straight and vertical, the motion of the engagement piece 40 can also be straight and vertical. However, in other embodiments these directions can vary.

Further, in some embodiments only one pin 44 and pin groove 46 can be provided. In such an embodiment, the engagement piece 40 can translate (with the pin 44) through the pin groove 46. The engagement piece 40 could additionally be able to rotate about the pin 44 within the groove 46. The engagement piece 40 could then rotate to better insure that both of the two projecting ends 42 contact the constrained article 1. For example, in embodiments where the article 1 is asymmetric or rests off-center from the engagement piece 1, it would be possible for only one projecting end 42 to contact the article 1, absent the ability to rotate. Thus, in some embodiments, only one pin-groove combination will be provided.

It will be understood that the depicted embodiment could also include 4 pins 44 and pin grooves 46, instead of only two. For example, an additional pair may be provided on an opposite side of the cross-section shown in FIGS. 3, 3A. This additional pair may be symmetric to the shown pair, such that a cross-section in the opposite direction would look substantially the same. Thus, in similar embodiments there may be two symmetrical pins 44 and pin grooves 46, which still allow rotation as described above. Similarly, in some embodiments there may be only one pin 44 that extends across the entire engagement piece 40 to enter two grooves 46 on opposite sides of the engagement piece 40. It will be understood that further variations are considered part of some embodiments of the inventions described herein. For example, in some embodiments the pin(s) can be provided on the first arm 12 and the groove(s) can be provided on the engagement piece 40.

Further, in some embodiments the engagement piece 40 can be biased to move towards an unlocked position (upward in the depicted embodiment) or towards a locked position. Such biasing can be provided, for example, by a spring such as a leaf spring. The spring can contact the pins 44, the main body of the engagement piece 40, or some other portion to bias the engagement piece 40. Biasing the engagement piece 40, in some embodiments, will advantageously facilitate insertion of an article 1, prior to securement.

The engagement piece 40 can be secured against the article 1 with the assistance of an actuator 60. The motion of the actuator 60 can be constrained in a similar manner as the motion of the engagement piece 40, using pins 64 and pin grooves 46 that can be positioned, shaped, substituted, and varied in similar ways. Notably, in the depicted embodiment only one pin 64 and groove 66 is shown. Further, as shown, the pin 64 is part of the first arm 12 and the groove 66 is part of the actuator 60. Additionally, the depicted embodiment includes a ramp 15 that can be molded into the first arm 12. As shown, the ramp 15 can provide a restraint against rotation of the actuator 60, and further reinforce its path of motion such that the actuator 60 can slide along the ramp 15. As best shown in FIGS. 2, 2A, the ramp 15 can be provided on opposite sides of the actuator 60, with a guideway 14 in the middle.

The guideway 14 can be part of the first arm 12, and can provide a further limitation on the path of both the actuator 60 and the engagement piece 40. More generally, the guideway 14 can provide a space for the actuator 60 and the engagement piece 40. Further, the walls of the guideway 14 can restrain the longitudinal movement of the actuator 60 and the engagement piece 40.

In operation, the actuator 60 can be pushed into the engagement piece 40 (downward in the depicted embodiment). In the depicted embodiment, such motion of the actuator 60 can be facilitated by a grip surface 62 on the top of the actuator 60. As is most clearly illustrated in FIG. 3, the actuator 60 includes an actuation surface 68. The actuation surface 68 contacts an actuation surface 48 of the engagement piece 40. This contact can then provide a force between the two pieces to push the engagement piece 40 into the cavity 26, and onto the article 1 to be secured. In other embodiments transmission of forces between the actuator 60 and the engagement piece 40 can be provided in other manners. For example, in some embodiments the actuator 60 and the engagement piece 40 can be physically connected, such that the actuator can retract the engagement piece 40. In another embodiment, the pieces can interact through magnetic forces. In even further embodiments, the pieces can become reversibly or irreversibly attached only upon initial contact.

In some embodiments, mechanisms may be provided to prevent the engagement piece 40 from moving to the unlocked position (e.g., upward in the depicted embodiment). For example, in some embodiments resistance from the article 1 itself may push the engagement piece 40 away. In other embodiments, the action of a spring biasing the engagement piece 40 out of the cavity 26 may provide a similar effect. Thus, in some embodiments a ratcheting mechanism can be provided between the actuator 60 or the engagement piece 40 and the first arm 12 to resist such movement. In other embodiments, frictional resistance can be provided between the actuator 60 or the engagement piece 40 and the first arm 12 to resist such movement absent a higher force. In even further embodiments, an additional device or feature can be provided to restrain the actuator 60 or the engagement piece 40 such as a latch, a magnetic force, an adhesive, a tie, or the like.

Further, as depicted, the engagement piece 40 can comprise two or more projecting ends 42, forming a multipronged structure. Advantageously, a two-pronged structure, in combination with the second arm 16 (e.g., the groove 18 thereof), can provide for three points of contact with the article 1 (one on each projecting end 42, and a third on the second arm 16). Such a 3-point securement system can constrain a wide variety of articles of varying shape and size.

Additionally, as best depicted in FIGS. 4-5A, in some embodiments a central axis through the channel or cavity 26 of the securement device 10 is not parallel to the external surface 20 of the securement device 10. Such an arrangement provides an incident angle for the article 1 to enter the patient's skin. For example, as depicted, a portion of the second arm 16 facing the cavity (e.g., the groove 18) is an angle with respect to the external surface 20.

The desired angle between the article 1 and the patient is created by angling the axis of the channel or cavity 26. This angle is selected in order to align the axis of the channel or cavity 26 of the device 10 with the desired incident angle with which the medical article is to contact the skin of the patient. A variety of different angles can be used, ranging from 0° to 45°, and more preferably from so to 25°. For instance, for the securement of intravenous catheters, it is desirable for the angle of incidence of the catheter to the skin of the patient to be between about 7° to about 15°. For the securement of arterial catheters, it is desirable for the angle of incident of the catheter to the skin of the patient to be about 12.5°. By angling the axis of the channel or cavity 26 at the desired angle, which will depend upon the particular securement application (e.g., securing an arterial catheter, an intravenous catheter, etc.), the proper angle of incidence for a catheter can be maintained.

Similarly, as shown, the surfaces of the projecting ends 42 can also be provided at an angle. In some embodiments this angle can match the angle of the axis through the cavity or channel 26.

The securement device 10 can optionally include one or more timers. The timer is disposed on the securement device 10 so as to be accessible by the healthcare provider. In some embodiments, the timer is disposed on an outer surface of the securement device 10 and optionally includes a display. By way of example, the display can be included or integrated with additional electronics 100 or other ancillary elements on the securement device 10.

The timer may be configured to measure elapsed time and can be activated manually by a user, remotely by a user, and/or by a triggering event. For example, the connection of one or more medical articles to the securement device 10 and/or the passage of fluid through a lumen in the securement device 10 can activate the timer. The timer indicates a time-based characteristic of the medical article or line, such as, for example, the length of time the medical article or line has been in place on the patient. In some implementations, the timer measures a flow rate of fluid into the patient and compares the measured flow rate to a target flow rate. Thus, the timer may be used to verify that lumens of the medical lines, securement device, and/or catheter are not occluded or partially occluded.

The timer can be flexible or rigid, and can be disposed directly on the securement device 10. In some embodiments, the timer is disposed on the anchor pad 80 (possibly with other ancillary elements). By prominently positioning the timer, the timer can provide an easy-to-use and reliable visual indicator of elapsed time. The timer can be a battery-operated timer or a chemically-active timer. Embodiments of a chemically active timer can change color or provide another visual response when exposed to air or a selected chemical for a given length of time.

In some implementations, the timer is activated by a healthcare provider at generally the same time the provider begins passing a fluid through the secured article 1. The activated timer may then provide a visual indication of the length of time elapsed or period since the catheter was connected to the securement device 10. The timer may provide, in addition to or instead of a visual response, an audible indication or alarm of a given length of time. For example, the timer may beep, chirp, or otherwise emit sound.

The period between indication outputs from the timer can be fixed or variable. For example, the timer can provide an indication after a first time period and then provided a second indication after a second time period. The first and second time periods may have the same or different durations. The first indication may be the same or different than the second indication. For example, the timer can provided an audible indication after the first time period and a visual indication after the second time period. Thus, the timer can be used to signal when the medical line should be replaced and/or re-sited.

The securement device 10 can optionally include one or more flow sensors or meters configured to sense a rate of fluid flow through the secured article 1 (e.g., as one of the above-referenced ancillary features, optionally provided with the electronics 100). In one embodiment the flow sensor detects flow using an optical sensor. The sensor may rely in part on the size, shape, and/or cross-section of the channel 26 to determine the flow rate. For example, the securement device 10 can include a flow sensor to measure a rate of infusate flow through the article 1. The one or more flow sensors can be configured to provide an audible or visual indication or alarm when a flow rate through the constrained article 1 exceeds a given threshold or is below a given threshold. For example, a flow sensor can be configured to provide an audible alarm when a flow rate through the article 1 is below a certain threshold such that the patient is not receiving sufficient fluid or infusate delivery.

The optional timers and/or flow sensors can include stored memory elements including one or more libraries of stored settings. For example, drug or medication libraries with stored settings relating to each individual drug or medication can be stored on memory elements to provide threshold values to the optional timers and/or flow sensors. In some embodiments, such memory elements can be configured to trigger an audible or visual indication or alarm when a given dosage has been met and/or when a pressure or flow characteristic of a given infusate deviates from an expected value.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the disclosure and the claims that follow.

What is claimed is:

1. A retainer for securing a medical article to a patient, the retainer comprising:
   a first member defining a portion of a channel and including a receptacle, the channel configured to receive at least a portion of the medical article;
   a second member having a portion movably retained within a portion of the receptacle to move between a first position and a second position, the second member contacting a part of the received portion of the medical article when in the second position to inhibit longitudinal movement of the medical article through the channel; and
   an actuator configured to move the second member from the first position to the second position.

2. The retainer according to claim 1, wherein the second member extends into the channel when in the second position.

3. The retainer according to claim 1, wherein the receptacle extends through the first member.

4. The retainer according to claim 1, wherein the second member passes through the receptacle when the second member moves from the first position to the second position.

5. The retainer according to claim 1, wherein the first member surrounds the receptacle.

6. The retainer according to claim 1, wherein the first member comprises a first arm, a second arm, and a connecting portion.

7. The retainer according to claim 6, wherein the receptacle is disposed in the first arm.

8. The retainer according to claim 6, wherein the receptacle is disposed in the connecting portion.

9. The retainer according to claim 1, wherein the second member moves in a first direction between the first position and the second position and the actuator moves in a second direction different than the first direction.

10. The retainer according to claim 9, wherein the first direction is a radial direction with respect to a longitudinal axis through the channel.

11. The retainer according to claim 1, wherein the second member slidingly engages with the first member.

* * * * *